United States Patent
Dubovoy et al.

(10) Patent No.: US 11,186,489 B2
(45) Date of Patent: Nov. 30, 2021

(54) ZINC / AMINO ACID-FUNCTIONALIZED SILICA

(71) Applicant: Colgate-Palmolive Company, New York, NY (US)

(72) Inventors: Viktor Dubovoy, Cresskill, NJ (US); Tatiana Brinzari, Piscataway, NJ (US); Michael Stranick, Bridgewater, NJ (US); Long Pan, Somerset, NJ (US); Ravi Subramanyam, Belle Mead, NJ (US)

(73) Assignee: Colgate-Palmolive Company, New York, NY (US)

(*) Notice: Subject to any disclaimer, the term of this patent is extended or adjusted under 35 U.S.C. 154(b) by 11 days.

(21) Appl. No.: 16/206,671

(22) Filed: Nov. 30, 2018

(65) Prior Publication Data

US 2019/0169034 A1 Jun. 6, 2019

Related U.S. Application Data

(60) Provisional application No. 62/594,685, filed on Dec. 5, 2017.

(51) Int. Cl.
| | |
|---|---|
| *C01B 33/18* | (2006.01) |
| *A61K 8/25* | (2006.01) |
| *A61K 8/27* | (2006.01) |
| *A61K 8/44* | (2006.01) |
| *A61K 8/21* | (2006.01) |
| *A61Q 11/00* | (2006.01) |
| *A61K 8/02* | (2006.01) |

(52) U.S. Cl.
CPC ............ *C01B 33/18* (2013.01); *A61K 8/0279* (2013.01); *A61K 8/21* (2013.01); *A61K 8/25* (2013.01); *A61K 8/27* (2013.01); *A61K 8/44* (2013.01); *A61Q 11/00* (2013.01); *A61K 2800/412* (2013.01); *A61K 2800/622* (2013.01); *A61K 2800/651* (2013.01); *C01P 2004/61* (2013.01); *C01P 2006/12* (2013.01)

(58) Field of Classification Search
CPC ...... A61Q 11/00; C01B 33/18; A61K 8/0279; A61K 8/44; A61K 8/21; A61K 8/27; A61K 8/25; A61K 2800/651; A61K 2800/622; A61K 2800/412; C01P 2006/12; C01P 2004/61
See application file for complete search history.

(56) References Cited

U.S. PATENT DOCUMENTS

| | | |
|---|---|---|
| 3,538,230 A | 11/1970 | Pader et al. |
| 3,862,307 A | 1/1975 | Di Giulio |
| 3,937,807 A | 2/1976 | Haefele |
| 3,959,458 A | 5/1976 | Agricola et al. |
| 4,051,234 A | 9/1977 | Gieske et al. |
| 4,340,583 A | 7/1982 | Wason |
| 5,004,597 A | 4/1991 | Majeti et al. |
| 5,188,821 A | 2/1993 | Gaffar et al. |
| 5,192,531 A | 3/1993 | Gaffar et al. |
| 5,413,844 A | 5/1995 | Persello |
| 9,504,858 B2 * | 11/2016 | Yuan .................... A61K 31/555 |
| 9,757,316 B2 | 9/2017 | Pan et al. |
| 9,763,865 B2 | 9/2017 | Pan et al. |
| 9,943,473 B2 | 4/2018 | Pan et al. |
| 9,980,890 B2 | 5/2018 | Pan et al. |
| 10,105,303 B2 | 10/2018 | Pan et al. |
| 2006/0018966 A1 * | 1/2006 | Lin ......................... A61K 9/143 |
| | | 424/484 |
| 2010/0158822 A1 * | 6/2010 | Fahnestock .............. A61Q 5/12 |
| | | 424/49 |
| 2012/0029135 A1 | 2/2012 | Kim et al. |
| 2019/0015310 A1 | 1/2019 | Pan et al. |
| 2019/0015313 A1 | 1/2019 | Daep et al. |

FOREIGN PATENT DOCUMENTS

| | | |
|---|---|---|
| WO | 2014/098826 | 6/2014 |
| WO | 2017/117500 | 7/2017 |

OTHER PUBLICATIONS

International Search Report and the Written Opinion of the International Searching Authority issued in International Application PCT/US2018/063407 (dated Jun. 13, 2019).

* cited by examiner

Primary Examiner — Lezah Roberts

(57) ABSTRACT

Disclosed herein is zinc/amino acid functionalized silica, compositions comprising the same, and oral care methods and uses for such compositions.

18 Claims, No Drawings

ZINC / AMINO ACID-FUNCTIONALIZED SILICA

CROSS-REFERENCE TO RELATED APPLICATIONS

This application claims priority to and the benefit of U.S. Provisional Application No. 62/594,685, filed on Dec. 5, 2017, the contents of which are hereby incorporated by reference in its entirety.

BACKGROUND

Oral cavity bacteria are the primary cause of dental ailments, including caries, gingivitis, periodontitis, and halitosis. Oral bacteria form biofilms which are tightly adhered to the oral surfaces, especially the tooth enamel. With time, these biofilms calcify and turn into tartar, making them more difficult to remove from the tooth surface. Current at-home dental treatments, such as tooth brushing and mouth rinsing, can provide only limited benefit in preventing the growth of oral biofilm, or preventing the conversion of biofilm to plaque and tartar. The only effective way to remove plaque and tartar once it has formed is through costly, sometimes uncomfortable professional dental treatments such as root planing and scaling. It would be extremely beneficial to develop means of preventing the initial formation of oral bacterial biofilms and inhibiting the growth of oral cavity bacteria. Zinc salts such as zinc oxide, zinc citrate, and zinc gluconate, have been used in the art for their antibacterial effects, but they can sometimes present difficulties in formulating oral care compositions, or they can sometimes result in undesirable taste or mouthfeel.

Complexes between metal ions and amino acids are known. Some of these, especially complexes between divalent metal ions and basic amino acids, have seen use in the field of oral care for their ability to treat dentinal hypersensitivity. Certain complexes, such as zinc-bis(lysine)-halide and zinc-bis(arginine)-halide, have been discovered to form stable, homogenous aqueous solutions, which under certain conditions, can precipitate zinc hydroxide, zinc oxide and other zinc species. The formation of such species as zinc oxide and zinc hydroxide provides a means of delivering bioactive zinc to the tissues of the oral cavity. In addition, the precipitation of these salts has enabled oral care compositions comprising these complexes to effectively plug the dentinal tubules of the teeth that transmit sensations of hypersensitivity.

These stable, soluble zinc-amino acid-halide complexes have also been disclosed as effective oral anti-bacterial agents. When placed in oral care formulations, these complexes provide an effective concentration of zinc ions to the enamel, thereby protecting against erosion, reducing bacterial colonization and biofilm development, and providing enhanced shine to the teeth. These formulations have the added benefit that they do not exhibit the poor taste and mouthfeel, poor fluoride delivery, and poor foaming and cleaning associated with conventional zinc-based oral care products using soluble zinc salts.

Of particular interest are compositions comprising the zinc-amino acid-halide complex zinc-lysine-chloride complex, designated ZLC, which may be formed, for example, from a mixture of zinc oxide and lysine hydrochloride. ZLC has the chemical structure $[Zn(C_6H_{14}N_2O_2)_2Cl]^+Cl^-$, and may exist in solution of the cationic cation ($[Zn(C_6H_{14}N_2O_2)_2Cl]^+$) and the chloride anion, or may be a solid salt, e.g., a crystal, optionally in dihydrate form. Zinc lysine complex may also exist in a halide free complex, for example, $[Zn(C_6H_{14}N_2O_2)_2]^{2+}$. Zinc amino acid halide complexes, including zinc-lysine-chloride complexes, have been disclosed, e.g., in US 2015-0328118A1, US 2015-0335554A1, US 2015-0328110A1, and US 2015-0335553A1, the contents of each of which are hereby incorporated by reference in their entireties.

While oral care compositions comprising zinc-amino acid-halide complexes such as the ZLC complex are known, it has been challenging to formulate compositions comprising these complexes which have good long-term stability. It has been particularly difficult to formulate low-water dentifrice compositions comprising such complexes, because these compositions suffer from unacceptably high increases in viscosity during storage. This progressive thickening or gelation makes the composition unsuitable for consumer use. In some circumstances, there can also be difficulty formulating compositions comprising these complexes in the presence of anionic ingredients such as sodium lauryl sulfate (SLS). There is thus a need for improved oral care formulations comprising zinc-amino acid-halide complexes, such as ZLC complex.

Silica is typically the predominant ingredient found in dentifrice products, and it has a variety of functions, especially as an abrasive to promote cleaning efficiency and to help whiten the teeth, and as a thickening agent to help optimize the rheological characteristics of the dentifrice. Functionalization of silica with adsorbed active agents has become widespread in the academic literature, including in the fields of catalysis, drug delivering and sensing.

BRIEF SUMMARY

It has now been discovered that silica, such as small-particle silica, can be surface-functionalized with zinc-amino acid complexes to yield zinc/amino acid-coated silica particles. These functionalized silica particles provide the oral care benefits, including antibacterial efficacy and desensitization, that result from compositions comprising zinc-amino acid-halide complexes, but without the difficulties that can arise in formulating such compositions. The cationic zinc-amino acid complexes are adsorbed onto the highly porous, anionic surface of the silica particles, resulting in improved stability for the complexes as well as higher overall concentration of the metal complexes in the compositions.

The present disclosure provides zinc/amino acid-coated silica particles, methods of preparing said particles, oral care compositions comprising said particles, and methods of using such compositions for the prevention and/or treatment of conditions of the oral cavity. These compositions provide a variety of benefits on oral hygiene and oral health, including reduction and inhibition of acid erosion of the enamel, cleaning of the teeth, reduction of bacterially-generated biofilm and plaque, reduction of gingivitis, reduction of tooth hypersensitivity, inhibition of tooth decay and inhibition of the formation of cavities. The methods comprise the application of a composition of the present disclosure to the teeth. The functionalized silica particles of the present disclosure can be formulated directly into various oral care delivery systems, such as liquid mouthwash, and both aqueous and non-aqueous gel or paste dentifrices. In some embodiments, the silica particles can be entrapped or encapsulated in various matrices for release during use of the composition.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The present disclosure provides, in a first aspect, zinc/amino acid-functionalized silica particles, for example, for use in oral care compositions. In preferred embodiments, the silica has an average particle size of 50 microns or less, for example, 20 microns or less. The functionalized silica particles are formed by incubating silica particles in an aqueous solution of zinc-amino acid-halide complex, followed by filtering and washing the silica particles. As used herein, "functionalized silica" means silica to which has surface-adsorbed zinc-amino acid complexes, such as zinc-lysine complexes, as provided herein.

In some embodiments, the silica used for functionalization is prophy silica. Prophy silicas are hydrated silicas having an average particle size of 5-20 microns. These include commercially available silicas such as Sylodent brand silicas from Grace Davison (e.g., Sylodent 783 silica) or Sorbosil brand silicas (e.g., Sorbosil AC77 silica). In some embodiments, suitable silicas for functionalization include those having an oil absorption value of 25 to 150 cc/100 g, e.g., 50 to 100, or about 75 cc/100 g. In some embodiments, suitable silicas have a particle size of 5 to 20 microns, or 8 to 20 microns, or 10 to 20 microns or 14 to 20 microns, or 16 to 18 microns, or about 16 microns. In some embodiments, suitable silicas have a moisture content, measured at 105° C. of 5 to 40% by weight, e.g., 10 to 30%, or 15 to 30%, or 20 to 30%, or about 25%. In some embodiments, the silica has a radioactive dentin abrasion (RDA) value of 100 to 150, e.g., about 125.

Other possible silicas for functionalization include typical abrasive silicas, such as precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 105, 114, 115, 119 and 165. Some of these silica abrasives are described in U.S. Pat. No. 4,340,583, incorporated herein by reference. In certain embodiments, abrasive materials useful in the practice of the oral compositions in accordance with the invention include silica gels and precipitated amorphous silica having an oil absorption value of less than 100 cc/100 g silica and in the range of 45 cc/100 g to 70 cc/100 g silica. Oil absorption values are measured using the ASTA Rub-Out Method D281. Low oil absorption silica abrasives useful include those marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight and an oil absorption of less than 70 cc/100 g of silica is an example of a low oil absorption silica abrasive useful in the present disclosure. Other possible silicas include small-particle silicas, such as those having an average particle size of 8 microns or less. This includes SORBOSIL AC43 silica, available from PQ Corporation (formerly from INEOS). SORBOSIL AC43 is a silica with properties including a powder RDA of 160, an oil absorption coefficient of 75 cm3/100 g, a weight mean particle size of 3.5 microns, an ignition loss at 1000° C. of 11.0% max, and a pH of 5.5. Another useful silica is silica with properties including an average particle size of 2.7-4.0 microns (as determined by MALVERN MASTERSIZER), a sieve residue of +45 μm, a moisture loss at 105° C. of 8.0% max, an ignition loss at 1000° C. of 14.0% max, and a pH of 5.5-7.5 in aqueous suspension), available from Ineos Silicas, Warrington, United Kingdom. Another embodiment of the invention is a silica with an average particle size of 1.5-6.0 microns.

In some embodiments, the functionalized silica comprises silica of an average particle size of less than 50 microns, for example, less than 20 microns, 1-50 microns, 1-20 microns, 1-16 microns, 4-16 microns, 8-16 microns, 10-20 microns, 12-20 microns, 14-20 microns, 14-18 microns, or about 16 microns, or a combination thereof (e.g., a population consisting of silica of 2-8 micron average size and 12-20 micron average size). As used herein throughout, references to silica size, surface area, porosity and other physical characteristics refer to the said characteristics of the silica particles in absence of the functionalization.

Surface area is an important characteristic in determining the extent to which zinc/amino acid complexes will adsorb onto the silica. In some embodiments, the silica particles used in preparation of the functionalized silica have an $N_2$ BET surface area of at least 25 $m^2/g$, or at least 50 $m^2/g$, or at least 100 $m^2/g$, or at least 500 $m^2/g$. In some embodiments, the silica particles have an $N_2$ BET surface area of 200-1200 $m^2/g$, or 400 to 1000 $m^2/g$, or 500 to 1000 $m^2/g$, or 500 to 800 $m^2/g$, or 600 to 1200 $m^2/g$, or 600 to 800 $m^2/g$, or about 700 $m^2/g$.

In some preferred embodiments, the silica particles used in preparation of the functionalized silica have an $N_2$ BET surface area of 500 to 1000 $m^2/g$ or 600 to 800 $m^2/g$ and an average particle size of 10-20 microns or 14 to 18 microns. In a particular embodiment, the silica has an $N_2$ BET surface area of 600 to 800 $m^2/g$ and an average particle size of 14 to 18 microns, for example, an $N_2$ BET surface area of about 700 $m^2/g$ and an average particle size of about 16 microns.

The zinc-amino acid-complexes used in the preparation of the functionalized silica of the present invention can be any of the zinc-amino acid complexes disclosed in U.S. Patent Application Publications 2015/0328117, 2015/0335553, and 2015/0328110, the contents of each of which are hereby incorporated by reference in their entireties. In some embodiments, the zinc-amino acid complex is a zinc-lysine-chloride complex, for example, the complex designated ZLC, which may be formed from a mixture of zinc oxide and lysine hydrochloride. ZLC has the chemical structure [Zn$(C_6H_{14}N_2O_2)_2$Cl]$^+$Cl$^-$, and may exist in solution of the cationic cation ([Zn$(C_6H_{14}N_2O_2)_2$Cl]$^+$) and the chloride anion, or may be a solid salt, e.g., a crystal, optionally in mono- or dihydrate form.

Loading of zinc/amino acid on the silica can range from about 0.1 mg/100 mg silica (0.1 wt %) to 30 mg/100 mg silica (30 wt %). In some embodiments, the loading ranges from about 5 wt % to about 30 wt %, or from 10 wt % to about 25 wt %, or from about 15 wt % to about 20 wt %, e.g., about 17 wt %. In some embodiments, the molar ratio of zinc to amino acid in the functionalized silica is from 5:1 to 1:5, e.g., from 4:1 to 1:4, or from 3:1 to 1:3, or from 2:1 to 1:2. In other embodiments, the ratio of zinc to amino acid in the functionalized silica is from 1:1 to 1:5, or 1:1 to 1:4, or 1:1 to 1:3, or 1:1 to 1:2, or about 1:3 or about 1:2.

In some embodiments, the functionalized silica is adsorbed with cationic zinc-amino acid complexes, for example, cationic zinc lysine complexes. Without being bound by theory, it is believed that zinc-amino acid complexes, including zinc-amino acid-halide complexes, become electrostatically surface-bound within the pores of the anionic silica particles. The actual species which are surface-bound to the silica may include complexes of the form $[Zn(AA)_3X]^+$, $[Zn(AA)_2X]^+$, $[Zn(AA)X]^+$, $[Zn(AA)_3]^{2+}$, $[Zn(AA)_2]^{2+}$, $[Zn(AA)]^{2+}$, and the like, wherein AA is an amino acid, preferably a basic amino acid, such as lysine or arginine, and wherein X is a halide, such as fluoride, chloride, bromide or iodide, or some other monovalent anion, such as hydroxide. Mixtures of different species may also be bound to the silica, and there may also be bound to the silica isolated zinc cations ($Zn^{2+}$) and/or free amino acids (e.g., lysine or arginine).

In a second aspect, the present disclosure provides an oral care composition (Composition 1), such as a dentifrice, e.g., a toothpaste, comprising the functionalized silica particles, as described above. Such a composition may comprise from 0.1-50 wt % of functionalized silica particles, e.g., 1-50 wt %.

In additional embodiments, the present disclosure provides oral care compositions as follows:

1.1. Composition 1, wherein the composition further comprises a basic amino acid, e.g., lysine or arginine, in free or orally acceptable salt form.
1.2. Composition 1 or 1.1, wherein the composition further comprises a metal salt, e.g., zinc salt, copper salt or stannous salt (e.g., zinc oxide, zinc citrate, zinc lactate, zinc phosphate, or a combination thereof).
1.3. Any of the foregoing compositions in the form of a toothpaste, gel, mouthwash, powder, cream, strip (e.g., thin films), or gum.
1.4. Any of the foregoing compositions in an orally acceptable base, e.g., a mouthwash, gel, or dentifrice base.
1.5. Any of the foregoing compositions in the form of a dentifrice, wherein the functionalized silica particles are present in an effective amount to deliver zinc to the oral cavity, e.g., present in an amount of from 0.1 to 20% by weight of the composition, or 0.5 to 15%, 0.5 to 10%, 1 to 10%, 2 to 8%, 3 to 5%, or about 3%, or about 5% or about 8% or about 10%.
1.6. Any of the foregoing compositions, wherein the composition comprises a dentifrice base further comprising an abrasive, e.g., an effective amount of a silica abrasive, or calcium abrasive, e.g., 10-30%, e.g., about 20%.
1.7. Any of the foregoing compositions in the form of an oral gel, wherein the functionalized silica particles are present in an effective amount to deliver zinc to the oral cavity, e.g., present in an amount of from 0.1 to 20% by weight of the composition, or 0.5 to 15%, 0.5 to 10%, 1 to 10%, 2 to 8%, 3 to 5%, or about 3%, or about 5% or about 8% or about 10%.
1.8. Any of the foregoing compositions further comprising an effective amount of a fluoride ion source, e.g., providing 50 to 3000 ppm fluoride.
1.9. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.
1.10. Any of the preceding compositions comprising an effective amount of one or more alkali phosphate salts, e.g., sodium or potassium salts, e.g., selected from alkali dibasic phosphate and alkali pyrophosphate salts, e.g., alkali phosphate salts selected from sodium phosphate dibasic, potassium phosphate dibasic, tetrasodium pyrophosphate, tetrapotassium pyrophosphate, sodium tripolyphosphate, and mixtures of any of two or more of these, e.g., in an amount of 1-20%, e.g., 2-8%, e.g., ca. 5%, by weight of the composition.
1.11. Any of the foregoing compositions comprising buffering agents, e.g., phosphate buffers or citrate buffers, for example, sodium phosphate buffer (e.g., sodium phosphate monobasic, disodium phosphate and/or phosphoric acid).
1.12. Any of the foregoing compositions comprising a humectant, e.g., selected from glycerin, sorbitol, propylene glycol, polyethylene glycol, xylitol, and mixtures thereof, e.g. comprising at least 10%, e.g., 10-70%, or 20-50%, or 20-40%, e.g., 25-35% or 50-70%, of humectant or humectant mixture.
1.13. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount from about 0.3% to about 4.5% by weight, e.g. 1-2% sodium lauryl sulfate (SLS); and/or a zwitterionic surfactant, for example a betaine surfactant, for example cocamidopropyl betaine, e.g. in an amount of from about 0.1% to about 4.5% by weight, e.g. 0.5-2% cocamidopropyl betaine.
1.14. Any of the preceding compositions further comprising a viscosity modifying amount of one or more of polysaccharide gums, for example xanthan gum or carrageenan, silica thickener, and combinations thereof.
1.15. Any of the preceding compositions comprising gum, strips, or fragments.
1.16. Any of the preceding compositions further comprising flavoring, fragrance and/or coloring.
1.17. Any of the foregoing compositions comprising an effective amount of one or more antibacterial agents, for example comprising an antibacterial agent selected from halogenated diphenyl ether (e.g. triclosan), herbal extracts and essential oils (e.g., rosemary extract, tea extract, magnolia extract, magnolol, honokiol, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan, or cetylpyridinium chloride or magnolol or honokiol.

1.18. Any of the preceding compositions further comprising a whitening agent, e.g., a selected from the group consisting of peroxides, metal chlorites, perborates, percarbonates, peroxyacids, hypochlorites, and combinations thereof.

1.19. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example, calcium peroxyphosphate, sodium perborate, sodium carbonate peroxide, sodium peroxyphosphate, and potassium persulfate);

1.20. Any of the preceding compositions further comprising a physiologically or orally acceptable potassium salt, e.g., potassium nitrate or potassium chloride, in an amount effective to reduce dentinal sensitivity.

1.21. Any of the foregoing compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.

1.22. Any of the foregoing compositions, further comprising a non-ionic polymer, e.g. polyvinylpyrrolidone (PVP), for example linear or cross-linked PVP.

1.23. Any of the preceding compositions further comprising a breath freshener, fragrance or flavoring.

1.24. Any of the foregoing compositions, wherein the pH of the composition is approximately neutral, e.g., from pH 5 to 10, or from pH 6 to pH 8 e.g., about pH 7.

1.25. Any of the foregoing compositions, wherein the mucin is entrapped or encapsulated within a matrix in the oral care composition, for example, a polymer matrix (e.g., a matrix formed from any of the polymers described herein or any combination thereof).

As used herein, the term "dentifrice" includes both aqueous and non-aqueous toothpastes and tooth gels, mouthwashes (including structured mouthwashes), beads, films, flosses, tapes, and gums.

In another aspect, the present disclosure provides a method (Method 1) of treating a disease, disorder or condition of the oral cavity, comprising the step of administering to a patient in need thereof an oral care composition (Composition 1, et seq.) comprising functionalized silica particles to deliver zinc to the oral cavity. In specific embodiments, said patient suffers from a disease, disorder or condition of the oral cavity, such as gingivitis, periodontitis, halitosis, cavity formation, enamel erosion, and/or oral infection (e.g., oral candidiasis). For example, where Composition 1, et seq., is a toothpaste composition, Method 1 would comprise the steps of brushing the teeth with the toothpaste composition for a sufficient amount of time (e.g., from 1-4 minutes, preferably 2-4 minutes), followed by rinsing the oral cavity with water, optionally followed by rinsing the oral cavity with a mouthwash.

In some embodiments, Method 1 further provides effectiveness to reduce and inhibit acid erosion of the enamel, clean the teeth, reduce bacterially-generated biofilm and plaque, reduce gingivitis, inhibit tooth decay and formation of cavities, and reduce dentinal hypersensitivity.

In some embodiments, the present disclosure provide a method according to Method 1, which is effective for one or more of the following: (i) to reduce hypersensitivity of the teeth, (ii) to reduce plaque accumulation, (iii) to reduce or inhibit demineralization and promote remineralization of the teeth, (iv) to inhibit microbial biofilm formation in the oral cavity, (v) to reduce or inhibit gingivitis, (vi) to promote healing of sores or cuts in the mouth, (vii) reduce levels of acid producing bacteria, (viii) to increase relative levels of non-cariogenic and/or non-plaque forming bacteria, (ix) to reduce or inhibit formation of dental caries, (x) to reduce, repair or inhibit pre-carious lesions of the enamel, e.g., as detected by quantitative light-induced fluorescence (QLF) or electrical caries measurement (ECM), (xi) to treat, relieve or reduce dry mouth, (xii) to clean the teeth and oral cavity, (xiii) to reduce erosion, (xiv) to whiten teeth; (xv) to reduce tartar build-up, (xvi) to freshen the breath and/or treat or prevent halitosis, and/or (xvii) to promote systemic health, including cardiovascular health, e.g., by reducing the potential for systemic infection via the oral tissues, the method comprising applying any of Compositions 1, et seq. as described above to the oral cavity of a person in need thereof, e.g., one or more times per day. The present disclosure further provides Compositions 1, et seq. for use in any of these methods.

The present disclosure further provides the use an oral care composition (Use 1) comprising functionalized silica particles (e.g., Composition 1, et seq.) to deliver zinc to the oral cavity, for example, in Method 1, as described above. In some embodiments, the use of Composition 1, et seq., is effective in treating diseases, disorders or conditions of the oral cavity (e.g., gingivitis, periodontitis, halitosis, cavity formation, enamel erosion, or oral infection) or in disrupting the formation of plaque and bacterial biofilm. In specific embodiments, said use is effective to reduce and inhibit acid erosion of the enamel, clean the teeth, reduce bacterially-generated biofilm and plaque, reduce gingivitis, inhibit tooth decay and formation of cavities, and/or reduce dentinal hypersensitivity.

The oral care composition used in the present disclosure can be in the form of any oral care formulations, including a toothpaste, gel, mouthwash, powder, cream, strip, gum, bead, film, floss or any other known in the art. In some embodiments, the oral care composition used in the present disclosure is a toothpaste or oral gel. In some embodiments, the oral care composition is a liquid mouthwash, aqueous or non-aqueous gel or paste dentifrice. In some embodiments, the oral care composition is structured mouthwash.

In another aspect, the present disclosure provides the use of functionalized silica particles in the manufacture of an oral care composition for use in Method 1. Such use may be beneficial for the treatment and/or prevention of a disease or disorder of the oral cavity, as described elsewhere herein, caused by oral bacteria.

In some embodiments, the oral care compositions (Composition 1, et seq.) may further comprises a basic amino acid. Basic amino acids are known to have many beneficial effects in the treatment and prevention of oral care diseases and disorders, such as a reduction in cariogenic bacteria and/or an increase in arginolytic bacteria.

By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In certain embodiments, the amino acid is lysine. In other embodiments, the amino acid is arginine.

In certain embodiments, zinc is present in the oral care composition used in the present disclosure in an amount of 0.05 to 10% by weight of the composition. In other embodiments, the amount of zinc is at least 0.1, at least 0.2, at least 0.3, at least 0.4, at least 0.5, at least 1, at least 2, at least 3, or at least 4 up to 10% by weight of the composition. In other embodiments, the amount of the zinc is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, the oral care composition used in the present disclosure is anhydrous. By anhydrous, there is less than 5% by weight water, optionally less than 4, less than 3, less than 2, less than 1, less than 0.5, less than 0.1 down to 0% by weight water.

Active Agents:

The oral care composition used in the present disclosure may comprise various agents which are active to protect and enhance the strength and integrity of the enamel and tooth structure and/or to reduce bacteria and associated tooth decay and/or gum disease, including or in addition to the functionalized silica particles. Effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., about 0.1 to about 20 wt % (expressed as weight of free base), e.g., about 1 to about 10 wt % for a consumer toothpaste or about 7 to about 20 wt % for a professional or prescription treatment product. Fluoride where present may be present at levels of, e.g., about 25 to about 25,000 ppm, for example about 750 to about 2,000 ppm for a consumer toothpaste, or about 2,000 to about 25,000 ppm for a professional or prescription treatment product. Levels of antibacterial agents will vary similarly, with levels used in toothpaste being e.g., about 5 to about 15 times greater than used in mouthrinse.

Fluoride Ion Source:

The oral care composition used in the present disclosure may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments, the fluoride ion source includes stannous fluoride, sodium fluoride, sodium monofluorophosphate as well as mixtures thereof. In certain embodiments, the oral care composition described herein may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions described herein at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counterion in the salt.

Abrasives:

The oral care composition used in the present disclosure, e.g. Composition 1 et seq., may include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Foaming Agents:

The oral care composition used in the present disclosure also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the composition. Polyoxyethylene is also commonly known as polyethylene glycol ("PEG") or polyethylene oxide. The polyoxyethylenes suitable for this composition will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions. Where present, the amount of foaming agent in the oral care composition (i.e., a single dose) is about 0.01 to about 0.9% by weight, about 0.05 to about 0.5% by weight, and in another embodiment about 0.1 to about 0.2% by weight.

Surfactants:

The oral care composition used in the present disclosure may contain anionic surfactants, for example:

i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
ii. higher alkyl sulfates, such as sodium lauryl sulfate,
iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$.
iv. higher alkyl aryl sulfonates such as sodium dodecyl benzene sulfonate (sodium lauryl benzene sulfonate)
v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The oral care composition used in the present disclosure may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the compositions described herein, e.g., Composition 1, et seq., comprises sodium lauryl sulfate.

The surfactant or mixtures of compatible surfactants can be present in the compositions described herein in about 0.1% to about 5.0%, in another embodiment about 0.3% to about 3.0% and in another embodiment about 0.5% to about 2.0% by weight of the total composition.

Tartar Control Agents:

In various embodiments, the oral care composition used in the present disclosure may comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The composition thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate $(Na_4P_2O_7)$, calcium pyrophosphate $(Ca_2P_2O_7)$, and sodium phosphate dibasic $(Na_2HPO_4)$, e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP)$(Na_5P_3O_{10})$, e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Polymers:

The oral care composition used in the present disclosure may also include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water-soluble alkali metal (e.g., potassium and sodium) or ammonium salts.

Silica thickeners, which form polymeric structures or gels in aqueous media, may be present in the oral care composition used in the present disclosure. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water-soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of about 0.5% to about 5.0% by weight of the total composition are used.

The oral care composition used in the present disclosure may include an anionic polymer, for example in an amount of from about 0.05 to about 5%. Such agents useful in compositions described herein are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Water:

The oral care composition used in the present disclosure may comprise significant levels of water. Water employed in the preparation of commercial oral compositions should be deionized and free of organic impurities. The amount of water in the compositions includes the free water which is added plus that amount which is introduced with other materials.

Humectants:

In certain embodiments, it is also desirable to incorporate in the oral care composition used in the present disclosure a humectant to prevent the composition from hardening upon exposure to air. Certain humectants can also impart desirable sweetness or flavor to dentifrice compositions. Suitable humectants include edible polyhydric alcohols such as glycerin, sorbitol, xylitol, propylene glycol as well as other polyols and mixtures of these humectants. In some embodiments of the composition described herein, the principal humectant is glycerin, which may be present at levels of greater than 25%, e.g. 25-35% about 30%, with 5% or less of other humectants.

Unless stated otherwise, all percentages of composition components given in this specification are by weight based on a total composition or formulation weight of 100%.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1: Preparation and Analysis of Functionalized Silica

A fresh solution of zinc-lysine chloride (ZLC) complex, $[Zn(C_6H_{14}N_2O_2)_2Cl]^+Cl^-$, is prepared by dissolving 2 moles of lysine hydrochloride (365 g) in 1 liter of deionized water to yield a clear solution, followed by slow addition of 1 mole of zinc oxide (81 g) with stirring. After stirring overnight at room temperature, the resulting suspension is centrifuged, decanted, and filtered to remove unreacted zinc oxide. The pH of the filtered solution is about 7.

1.50 g of Sylodent 783 silica is degassed at 100° C. for one hour, and this was combined with 15 g of the ZLC solution, and stirred overnight at room temperature. The mixture is then filtered, the silica is washed with 1 liter of deionized water and dried in an oven at 50° C. overnight to yield Silica A.

A comparative lysine-functionalized silica is also prepared. 1.50 g of the degassed Sylodent silica is stirred overnight at room temperature in 15 g of lysine hydrochloride solution (made by dissolving 18.2 g lysine hydrochloride in 50.5 g deionized water). The mixture is then filtered and the silica is washed with 1 liter of deionized water and dried in an oven at 50° C. overnight to yield Silica B.

Fourier Transform Infrared Spectroscopy (FTIR):

Infrared spectra are collected using a Bruker Vertex 70 FTIR spectrometer (Bruker Optics, Billerica, Mass.) equipped with a GladiATR diamond ATR accessory (Pike technologies, Madison, Wis.). The spectral range is 80-4000 $cm^{-1}$ and a resolution of 4 $cm^{-1}$ is used. All measurements are carried out at room temperature on as prepared powdered samples of Silica A, Silica B and un-functionalized Sylodent 783 silica.

FTIR-ATR spectra of the three silicas show clear spectral differences. Compared to the pure Sylodent silica and Silica B, Silica A displays modification to the silica local structure as manifested by the broadening and slight red shift of the main peak maximum of the $v_{as}$(Si—O) stretching vibration near 1050 $cm^{-1}$. This suggests an increased distribution and/or weakening of the Si—O bonding in Silica A. In addition to changes in the silica features, a clear presence of lysine is observed in the Silica A sample. In contrast, the Silica B sample displays almost no lysine attached to $SiO_2$ and, overall, it closely resembles the pure Sylodent spectrum. This finding suggests that the Silica A sample contains lysine associated with or bound to zinc in some form of zinc-lysinate complex (effect of pH on adsorption of lysine cannot be completely ruled out).

XPS analyses are conducted using a Physical Electronics VeresaProbe II spectrometer (Ulvac PHI, Chanhassen, Minn.). Replicate analyses are conducted on the silica samples and the average elemental compositions (in atomic percent) are determined.

$N_2$ adsorption experiments, carried out at 77 K with sample pretreatment entailing 80° C. heating under $N_2$ atmosphere overnight, are also conducted to determine BET surface area and BJH pore size distributions. The original Sylodent silica exhibits an $S_{BET}$ of 663 $m^2/g$, a pore volume of 0.33 $cm^3/g$ and a pore size distribution of 0.6 to 3 nm. The functionalized Silica A shows an $S_{BET}$ of 214 $m^2/g$ and a pore volume of 0.12 $cm^3/g$, with a pore size distribution of about 1.6 nm. Thus, the surface area and pore volume are reduced by 67.7% and 63.6%, respectively, indicating that the pores are partially filled with the zinc/lysine complexes.

Elemental analysis is shown in the Table below. The figures for ICP and CHN are shown in weight percent, while the figures for XPS are shown in atomic percent.

| Analysis | Sample | Zn | Si | Cl | C | H | N |
| --- | --- | --- | --- | --- | --- | --- | --- |
| ICP-OES | Silica A | 8.1 | 46.1 | — | — | — | — |
| XPS | Silica A | 2.1 | 24.2 | 0.2 | 10.0 | — | 2.2 |
| XPS | Silica B | — | 30.0 | — | 1.0 | — | 0.3 |
| CHN | Silica A | — | — | — | 5.1 | 2.5 | 1.9 |
| CHN | Silica B | — | — | — | 0.4 | 2.5 | 0.1 |

ICP-OES elemental analysis of Silica A indicates 8.10 and 46.12 wt. % of zinc (Zn) and silicon (Si), respectively. XPS analysis is a key diagnostic tool to elucidate the nature and concentration(s) of elements on the surface of the materials. The analysis shows that: 1) the concentration of carbon in the form of COO— was 1.1 atom % in Silica A, indicating the presence of lysine on the surface; 2) the total amount of nitrogen was 2.2 atom % in Silica A, further indicating the presence of lysine on the silica surface; 3) very low levels of C and N are observed for Silica B, indicating that lysine alone does not adsorb to silica to any meaningful extent; 4) for Silica A, the ratio of N total/Zn was measured at 1.0, which suggests either that some ZLC complex degraded during the water wash or that the ZLC complex transformed into another molecular moiety (e.g., Lys-Zn—$SiO_2$); and 5) the Auger parameter of Zn in the Silica A sample (2008.7 eV) resembles that of chemisorbed Zn (2008.8 eV) instead of either ZLC complex (2009.2 eV) or zinc oxide (2010.0 eV). It is important to note that XPS is a surface analysis tool and can only provide diagnostic information for the surface (~20 nm) layer of a material.

Example 2: Alamar Blue Antibacterial Assay

Human saliva generated is diluted 4× volumetrically, centrifuged and decanted to produce a translucent solution of oral care bacterial flora. 5 mL of saliva solution is combined with Silica A or deionized water. The samples are incubated in a 37° C. oven for 1 hour under 100 RPM shaking. The samples are then removed and 200 μL Alamar Blue dye is added to each. The samples are then returned to the oven. The control sample consists of 5 mL of freshly prepared saliva solution and 33.6 mg of deionized water. The Silica A sample consists of 5 mL of freshly prepared saliva solution and 101.9 mg of Silica A. Alamer blue (resazurin) is an indicator dye used to show cell viability in assays. The native dye is blue, but in the presence of microbial aerobic respiration products, the dye irreversibly becomes converted to the red resorufin species. It is found that the deionized water control is bright red, indicating the presence of bacteria, while the Silica A sample remains dark blue, indicating no significant presence of viable bacteria. This demonstrates the antibacterial action of Silica A.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

What is claimed:

1. A functionalized silica particle comprising a prophy silica having an average particle size of 5 to 20 microns; and a zinc-amino acid complex adsorbed to a surface of said silica, wherein the zinc-amino acid complex comprises zinc-lysine complex and/or zinc-arginine complex having a structure selected from one or more of $[Zn(AA)_3X]^+$, $[Zn(AA)_2X]^+$, $[Zn(AA)X]^+$, $[Zn(AA)_3]^{2+}$, $[Zn(AA)_2]^{2+}$, $[Zn(AA)]^{2+}$, wherein AA is lysine or arginine and wherein X is a halide, or another monovalent anion.

2. The functionalized silica particle according to claim 1, wherein the zinc-amino acid complex comprises zinc-lysine complex having a structure selected from one or more of $[Zn(AA)_3X]^+$, $[Zn(AA)_2X]^+$, $[Zn(AA)X]^+$, $[Zn(AA)_3]^{2+}$, $[Zn(AA)_2]^{2+}$, $[Zn(AA)]^{2+}$, wherein AA is lysine, and wherein X is a halide or another monovalent anion.

3. The functionalized silica particle according to claim 1, wherein the zinc-amino acid complex comprises zinc-arginine complex having a structure selected from one or more of $[Zn(AA)_3X]^+$, $[Zn(AA)_2X]^+$, $[Zn(AA)X]^+$, $[Zn(AA)_3]^{2+}$, $[Zn(AA)_2]^{2+}$, $[Zn(AA)]^{2+}$, wherein AA is arginine, and wherein X is a halide, or another monovalent anion.

4. The functionalized silica particle according to claim 2 wherein X is chloride.

5. The functionalized silica particle according to claim 1, wherein the silica has an $N_2$ BET surface area of 200-1200 $m^2/g$.

6. The functionalized silica particle according to claim 1, wherein the silica has an $N_2$ BET surface area of 600 to 800 $m^2/g$ and an average particle size of 14 to 18 microns.

7. The functionalized silica particle according to claim 1, wherein the functionalized silica contains from 0.1 to 10 mg of zinc/amino acid per 100 mg of silica.

8. The functionalized silica particle according to claim 1, comprising from about 0.1 wt % to about 30 wt % zinc/amino acid, optionally wherein the zinc to amino acid molar ratio is from 5:1 to 1:5.

9. An oral care composition comprising a functionalized silica particle according to claim 1.

10. The oral care composition according to claim 9, wherein the composition comprises from 0.1 to 50% by weight of functionalized silica particles.

11. The oral care composition according to claim 9, further comprising a metal salt.

12. The oral care composition according to claim 11, wherein the metal salt comprises zinc oxide, zinc citrate, zinc lactate, zinc phosphate, or a combination thereof.

13. The oral care composition according to claim 9, further comprising a basic amino acid, in free or orally acceptable salt form.

14. The oral care composition according to claim 9, in the form of a toothpaste, gel, mouthwash, powder, cream, strip, thin film, or gum.

15. The oral care composition according to claim 14, in the form of a toothpaste, gel or mouthwash.

16. The oral care composition according to claim 9, further comprising an effective amount of a fluoride ion source.

17. A method of treating a disease, disorder or condition of the oral cavity, comprising the step of administering to a patient in need thereof an oral care composition according to claim 9, to deliver zinc to the oral cavity, optionally, wherein said patient suffers from a disease, disorder or condition of the oral cavity, such as gingivitis, periodontitis, halitosis, cavity formation, enamel erosion, and/or oral infection.

18. The functionalized silica particle according to claim 4, wherein the functionalized silica is made by incubating silica particles in an aqueous solution of a zinc-amino acid-halide complex having the structure $[Zn(lysine)_2Cl]^+$ $Cl^-$.

* * * * *